(12) United States Patent
Moloney et al.

(10) Patent No.: US 11,957,833 B2
(45) Date of Patent: Apr. 16, 2024

(54) ELECTRONIC AEROSOL PROVISION SYSTEM

(71) Applicant: NICOVENTURES TRADING LIMITED, London (GB)

(72) Inventors: Patrick Moloney, London (GB); Colin Dickens, London (GB); Justin Han Yang Chan, London (GB)

(73) Assignee: NICOVENTURES TRADING LIMITED, London (GB)

( * ) Notice: Subject to any disclaimer, the term of this patent is extended or adjusted under 35 U.S.C. 154(b) by 754 days.

(21) Appl. No.: 15/733,583

(22) PCT Filed: Feb. 12, 2019

(86) PCT No.: PCT/GB2019/050364
§ 371 (c)(1),
(2) Date: Sep. 4, 2020

(87) PCT Pub. No.: WO2019/171017
PCT Pub. Date: Sep. 12, 2019

(65) Prior Publication Data
US 2021/0000184 A1    Jan. 7, 2021

(30) Foreign Application Priority Data

Mar. 7, 2018 (GB) ..................... 1803648

(51) Int. Cl.
*A61M 15/06* (2006.01)
*A24F 40/05* (2020.01)
(Continued)

(52) U.S. Cl.
CPC ............ *A61M 15/06* (2013.01); *A24F 40/05* (2020.01); *A24F 40/50* (2020.01); *A24F 40/57* (2020.01);
(Continued)

(58) Field of Classification Search
CPC ......... A61M 15/06; A24F 40/10; A24F 40/50; A24F 40/51; A24F 40/57; A24F 40/65; G05B 19/042; G05B 2219/25286
(Continued)

(56) References Cited

U.S. PATENT DOCUMENTS

| 4,358,665 A | 11/1982 | Owen |
| 4,523,084 A | 6/1985 | Tamura et al. |

(Continued)

FOREIGN PATENT DOCUMENTS

| CN | 1500546 A | 6/2004 |
| CN | 101522244 A | 9/2009 |

(Continued)

OTHER PUBLICATIONS

International Search Report, International Application No. PCT/GB2019/050364, dated Apr. 23, 2019, 2 pages.
(Continued)

*Primary Examiner* — Peter G Leigh
(74) *Attorney, Agent, or Firm* — Husch Blackwell LLP (57) ABSTRACT

An electronic vapor provision system includes a vaporizer for vaporizing a payload for inhalation by a user of the electronic vapor provision system, the vaporizer taking a finite period of time from having power supplied to it to vaporize the payload; a power supply for supplying power to the vaporizer to vaporize the payload in response to a user activation; one or more sensors operable to output respective signals in response to interaction of the user with the electronic vapor provision system; an estimation processor configured to estimate a user's expected moment of activation, based upon analysis of one or more of the respective signals; and a control processor configured to cause power to be supplied to the vaporizer at a time that precedes the user's estimated expected moment of activation.

19 Claims, 6 Drawing Sheets

(51) Int. Cl.
  *A24F 40/50* (2020.01)
  *A24F 40/57* (2020.01)
  *A24F 40/65* (2020.01)
  *G05B 19/042* (2006.01)
  *A24F 40/10* (2020.01)

(52) U.S. Cl.
  CPC ............ *A24F 40/65* (2020.01); *G05B 19/042* (2013.01); *A24F 40/10* (2020.01); *G05B 2219/25286* (2013.01)

(58) Field of Classification Search
  USPC .......................................................... 131/328
  See application file for complete search history.

(56) References Cited

U.S. PATENT DOCUMENTS

| | | |
|---|---|---|
| 4,947,874 A | 8/1990 | Brooks et al. |
| 5,095,921 A | 3/1992 | Losee et al. |
| 5,372,148 A | 12/1994 | McCafferty et al. |
| 5,434,386 A | 7/1995 | Glenn et al. |
| 5,894,841 A | 4/1999 | Voges |
| 6,766,220 B2 | 7/2004 | McRae et al. |
| 7,147,170 B2 | 12/2006 | Nguyen et al. |
| 8,079,371 B2 | 12/2011 | Robinson et al. |
| 8,511,318 B2 | 8/2013 | Hon |
| 2003/0205229 A1 | 11/2003 | Crockford et al. |
| 2004/0081624 A1 | 4/2004 | Nguyen et al. |
| 2005/0274193 A1 | 12/2005 | Kwon et al. |
| 2006/0130860 A1 | 6/2006 | Cholet |
| 2007/0045288 A1 | 3/2007 | Nelson |
| 2007/0074734 A1 | 4/2007 | Braunshteyn et al. |
| 2007/0113665 A1 | 5/2007 | Johnson |
| 2009/0095312 A1 | 4/2009 | Herbrich et al. |
| 2010/0024517 A1 | 2/2010 | Ratner |
| 2010/0236546 A1 | 9/2010 | Yamada et al. |
| 2010/0242974 A1 | 9/2010 | Pan |
| 2011/0226236 A1 | 9/2011 | Buchberger |
| 2011/0265806 A1 | 11/2011 | Alarcon et al. |
| 2012/0048266 A1 | 3/2012 | Alelov |
| 2012/0199146 A1 | 8/2012 | Marangos |
| 2012/0227752 A1 | 9/2012 | Alelov |
| 2012/0234821 A1 | 9/2012 | Shimizu |
| 2012/0242974 A1 | 9/2012 | LaValley et al. |
| 2012/0298220 A1 | 11/2012 | Hidaka et al. |
| 2013/0319440 A1 | 12/2013 | Capuano |
| 2014/0278258 A1 | 9/2014 | Shafer |
| 2014/0299125 A1 | 10/2014 | Buchberger |
| 2014/0334804 A1 | 11/2014 | Choi |
| 2015/0136153 A1 | 5/2015 | Lord |
| 2015/0142387 A1 | 5/2015 | Alarcon et al. |
| 2015/0245660 A1 | 9/2015 | Lord |
| 2015/0257448 A1 | 9/2015 | Lord |
| 2015/0313284 A1 | 11/2015 | Liu |
| 2016/0206003 A1 | 7/2016 | Yamada et al. |
| 2016/0242466 A1 | 8/2016 | Lord et al. |
| 2016/0262456 A1 | 9/2016 | Borkovec et al. |
| 2016/0309787 A1* | 10/2016 | Hawes .................... A24F 40/42 |
| 2017/0035114 A1 | 2/2017 | Lord |
| 2017/0108840 A1 | 4/2017 | Hawes et al. |
| 2017/0238596 A1 | 8/2017 | Matsumoto et al. |
| 2017/0311845 A1 | 11/2017 | Cho et al. |
| 2017/0368273 A1 | 12/2017 | Rubin |
| 2020/0154770 A1 | 5/2020 | Hepworth et al. |

FOREIGN PATENT DOCUMENTS

| | | | |
|---|---|---|---|
| CN | 101524187 A | 9/2009 | |
| CN | 100566769 C | 12/2009 | |
| CN | 201830899 U | 5/2011 | |
| CN | 102322893 A | 1/2012 | |
| CN | 104366695 A * | 2/2015 | ............ A24F 40/40 |
| CN | 104470388 A * | 3/2015 | ........... A24F 47/008 |
| CN | 104544570 A | 4/2015 | |
| EP | 0430559 A2 | 6/1991 | |
| EP | 0516293 A1 | 12/1992 | |
| EP | 1785711 A2 | 5/2007 | |
| EP | 1989946 A1 | 11/2008 | |
| EP | 2047880 A1 | 4/2009 | |
| EP | 2119375 A1 | 11/2009 | |
| EP | 2340730 A1 | 7/2011 | |
| EP | 2468118 A1 | 6/2012 | |
| EP | 2908673 A2 | 8/2015 | |
| EP | 2989911 A1 * | 3/2016 | ............ A24F 40/50 |
| EP | 3125706 A1 | 2/2017 | |
| GB | 2518937 A * | 4/2015 | ............ A24F 40/50 |
| JP | S5640917 A | 4/1981 | |
| JP | S5640977 A | 4/1981 | |
| JP | H02124082 A | 5/1990 | |
| JP | H05212100 A | 8/1993 | |
| JP | H069233 U | 2/1994 | |
| JP | H08511966 A | 12/1996 | |
| JP | H112577 A | 1/1999 | |
| JP | 2000132654 A | 5/2000 | |
| JP | 3392138 B2 | 3/2003 | |
| JP | 2004177579 A | 6/2004 | |
| JP | 2005538159 A | 12/2005 | |
| JP | 2007192802 A | 8/2007 | |
| JP | 2008165769 A | 7/2008 | |
| JP | 2009525746 A | 7/2009 | |
| JP | 2010526553 A | 8/2010 | |
| JP | 2012506263 A | 3/2012 | |
| JP | 4933046 B2 | 5/2012 | |
| JP | 2012135299 A | 7/2012 | |
| JP | 5041550 B2 | 10/2012 | |
| JP | 2013524835 A | 6/2013 | |
| JP | 2014501106 A | 1/2014 | |
| JP | 2014504886 A | 2/2014 | |
| JP | 2015537195 A | 12/2015 | |
| KR | 20120089544 A | 8/2012 | |
| KR | 200464889 Y1 * | 2/2013 | ............ A24F 40/40 |
| KR | 101345358 B1 * | 12/2013 | ............ A24F 40/10 |
| RU | 107026 U1 | 8/2011 | |
| WO | 03095005 A1 | 11/2003 | |
| WO | 2007091181 A2 | 8/2007 | |
| WO | 2009069518 A1 | 6/2009 | |
| WO | 2010045670 A1 | 4/2010 | |
| WO | 2011067877 A1 | 6/2011 | |
| WO | 2011137453 A2 | 11/2011 | |
| WO | 2012109371 A2 | 8/2012 | |
| WO | 2015112750 A1 | 7/2015 | |
| WO | 2015131991 A1 | 9/2015 | |
| WO | 2015189556 A1 | 12/2015 | |

OTHER PUBLICATIONS

Written Opinion, International Application No. PCT/GB2019/050364, dated Apr. 23, 2019, 5 pages.

"Decision to Grant received for Japanese Patent Application No. 2018-086172, mailed on Dec. 8, 2020", 5 pages (2 pages of English Translation and 3 pages of Official Copy).

"Extended European Search Report received for European Patent Application No. 19164911.0, mailed on Jun. 24, 2019", 8 pages.

"International Preliminary Report on Patentability received for PCT Patent Application No. PCT/EP2013/071069, mailed on Apr. 28, 2015", 11 pages.

"International Preliminary Report on Patentability received for PCT Patent Application No. PCT/GB2017/050781, mailed on Feb. 27, 2018", 13 pages.

"International Preliminary Report on Patentability received for PCT Patent Application No. PCT/GB2018/051540, mailed on Sep. 10, 2019", 11 pages.

"International Preliminary Report on Patentability received for PCT Patent Application No. PCT/GB2019/050364, mailed on Sep. 17, 2020", 7 Pages.

"International Search Report and Written Opinion received for Application No. PCT/GB2017/050781 mailed Jun. 14, 2017", 12 pages.

"International Search Report and Written Opinion received for PCT Patent Application No. PCT/EP2013/071069, mailed on Dec. 20, 2013", 3 pages.

(56) References Cited

OTHER PUBLICATIONS

"International Search Report and Written Opinion received for PCT Patent Application No. PCT/GB2018/051540, mailed on Sep. 13, 2018", 7 pages.
"Japanese Office Action, Japanese Patent Application No. 2015-537195, mailed Mar. 15, 2016", 2 pages (Official Copy Only).
"Japanese Search Report, Application No. 2016-227701, dated Aug. 23, 2017", 40 pages.(26 pages of Official Copy and 14 pages of English Tranlsation).
"Korean Office Action, Application No. 10-2018-7035809, dated Jul. 24, 2019", 22 pages.(11 pages of English Translation and 11 Pages of Official Copy).
"Notice of Opposition received for European Patent Application No. 13774188.0, mailed on Feb. 19, 2020", 95 pages.
"Notice to File a Response received for Korean Patent Application No. 10-2020-7028087, mailed on Jan. 18, 2023", 7 pages (4 pages English Translation and 3 pages of Official Copy).
"Office Action and Search Report received for Chinese Patent Application No. 201380054420.1, mailed on Jun. 19, 2017", 19 pages.(8 pages of English Translation and 11 pages Official Copy).
"Office Action received for Brazilian Patent Application No. BR112020018205-2, mailed on Jan. 5, 2023", 4 pages (Official Copy Only).
"Office Action received for Chinese Patent Application No. 201380054420.1, mailed on Sep. 26, 2016", 17 pages (9 pages of English Translation and 8 pages of Official Copy).
"Office Action received for Chinese Patent Application No. 201710348338.X, mailed on Mar. 25, 2020", 17 pages (9 pages of English Translation and 8 pages of Official Copy Only).
"Office Action received for Chinese Patent Application No. 201980017447.0, mailed on Dec. 21, 2022", 14 pages (7 pages of English Translation and 8 pages of Official Copy).
"Office Action received for Japanese Patent Application No. 2018-086172, mailed on Feb. 3, 2020", 17 Pages (8 pages of English Translation and 9 pages of Official Copy).
"Office Action received for Korean Patent Application No. 10-2015-7010071, mailed on Oct. 17, 2016", 22 pages (13 pages of English Translation and 9 pages of Official Copy).
"Office Action received for Malaysian Patent Application No. PI2020004429, mailed on Jul. 14, 2023", 3 pages.
"Search Report and Decision to Grant received for Russian Patent Application No. 2015114090, mailed on Aug. 24, 2016", 14 pages (Official Copy Only).
"Search Report for Chinese Application No. 201910151850.4 mailed on Apr. 28, 2021", 2 pages of Official Copy.
Akbar, et al., "Temperature Compensation of Piezoresistive Pressure Sensors", Sensors and Actuators A, vol. 33, 1992, pp. 155-162.
Boge, Plabmann, "Handbuch Elektrotechnik", Wiesbaden, Germany: Vieweg Verlag, Ed. 3 ISBN: 3-528-24944-7, 2004, 6 pages.
Freescale Semiconductor, "100kPa On-Chip Temperature Compensated and Calibrated Silicon Pressure Sensors", 2008, 10 pages.
Freescale Semiconductor "Integradted Silicon Pressure Sensor On-Chip Signal Conditioned, Temperature Compensated and Calibrated", 2010, 18 pages.
Freescale Semiconductor, "Temperature Compensation Methods for the Motorola X-Ducer Pressure Sensor Element", 11 pages.
Leonhard, Stiny, "Grundwissen Elektrotechnik und Elektronik", Haag a. d. Am per, Germany: Springer Vieweg, Ed. 7 ISBN: 978-3-658-18318-9., 2018, 3 pages.
Lu, et al., "Photonic Crystal Based All-Optical Pressure Sensor", 2011, pp. 621-624.
Mozek, et al., "Digital Temperature Compensation of Capacitive Pressure Sensors", Informacije, vol. 40, 2010, pp. 38-44.
Silicon Microstructures, "Active Temperature Compensation and Calibration for MEMS Pressure Sensors with Constant Voltage", 6 pages.

\* cited by examiner

ELECTRONIC AEROSOL PROVISION SYSTEM

PRIORITY CLAIM

The present application is a National Phase entry of PCT Application No. PCT/GB2019/050364, filed Feb. 12, 2019, which claims priority from GB Patent Application No. 1803648.3, filed Mar. 7, 2018, each of which is hereby fully incorporated herein by reference.

FIELD

The present disclosure relates to electronic aerosol provision systems such as nicotine delivery systems (e.g. electronic cigarettes and the like).

BACKGROUND

Electronic aerosol provision systems such as electronic cigarettes (e-cigarettes) generally contain a reservoir of a source liquid containing a formulation, typically including nicotine, from which an aerosol is generated, e.g. through heat vaporization. Alternatively a gel, or a solid material such as processed or unprocessed tobacco leaf, may be similarly used to generate an aerosol through non-combustive heat vaporization. Hence more generally such a system may be referred to as containing a payload to be aerosolized. An aerosol source for an aerosol provision system may thus comprise a heater having a heating element arranged to receive or engage with the payload, for example through wicking/capillary action, or heat conduction. While a user inhales on the device, electrical power is supplied to the heating element to vaporize payload in the vicinity of the heater to generate an aerosol for inhalation by the user. Such devices are usually provided with one or more air inlet holes located away from a mouthpiece end of the system. When a user sucks on a mouthpiece connected to the mouthpiece end of the system, air is drawn in through the inlet holes and past the aerosol source. There is a flow path connecting between the aerosol source and an opening in the mouthpiece so that air drawn past the aerosol source continues along the flow path to the mouthpiece opening, carrying some of the aerosol from the aerosol source with it. The aerosol-carrying air exits the aerosol provision system through the mouthpiece opening for inhalation by the user.

Usually an electric current is supplied to the heater when a user is drawing/puffing on the device. Typically, the electric current is supplied to the heater, e.g. a resistance heating element, in response to either the activation of an airflow sensor along the flow path as the user inhales/draw/puffs or in response to the activation of a button by the user. The heat generated by the heating element is used to vaporize a formulation. The released vapor mixes with air drawn through the device by the puffing consumer and forms an aerosol. When the user has finished the puff (drop of air flow/drop of pressure) the flow or pressure sensor deactivates the electric heater by cutting off the electric current.

However, in order to provide a responsive experience it is necessary to provide rapid vaporization of the payload when the system is activated by the user, and this in turn requires rapid activation of the heater. However, this depletes the battery in the system more quickly than would occur if the heater could be activated more slowly. Furthermore, rapid activation of the heater militates against certain types of heater being used, such as for example a heater with a resistance heating element distanced from the payload, and with the generated heat transferred to the payload over a finite period of time via heat flow along a thermal conductor.

Various approaches are described which seek to help address some of these issues.

SUMMARY

In a first aspect, an electronic vapor provision system is provided in accordance with this disclosure.

In another aspect, a method of vapor provision is provided in accordance with this disclosure.

It will be appreciated that features and aspects of the disclosure described above in relation to the first and other aspects of the disclosure are equally applicable to, and may be combined with, embodiments of the disclosure according to other aspects of the disclosure as appropriate, and not just in the specific combinations described above.

BRIEF DESCRIPTION OF THE DRAWINGS

Embodiments of the disclosure will now be described, by way of example only, with reference to the accompanying drawings, in which.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to an aerosol provision system, such as an e-cigarette. Throughout the following description the term "e-cigarette" is sometimes used but this term may be used interchangeably with aerosol (vapor) provision system.

Figure 1:
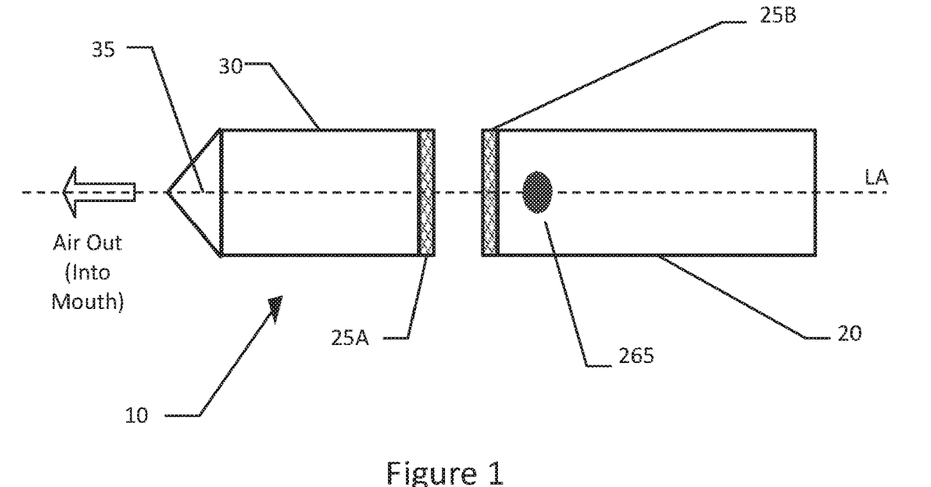
FIG. 1 is a schematic (exploded) diagram of an electronic vapor provision system such as an e-cigarette in accordance with some embodiments of the disclosure.

FIG. 1 is a schematic diagram of an electronic vapor provision system such as an e-cigarette 10 in accordance with some embodiments of the disclosure (not to scale). The e-cigarette has a generally cylindrical shape, extending along a longitudinal axis indicated by dashed line LA, and comprises two main components, namely a body 20 and a cartomizer 30. The cartomizer includes an internal chamber containing a payload such as for example nicotine in a solution, gel or foam matrix form, or a block of botanical material, a vaporizer (such as a heater), and a mouthpiece 35. References to 'nicotine' hereafter will be understood to be merely exemplary and can be substituted with any suitable active ingredient. Similarly references to 'reservoir' can be considered synonymous to any suitable payload. The payload can take the form of any suitable structure for retaining the nicotine until such time that it is required to be delivered to the vaporizer. It should also be appreciated that in other implementations the payload may directed be received in the device (as opposed to being stored within the cartomizer 30). For example, the payload may take the form of a tobacco rod wrapped in paper or similar material, or the payload may be deposited on a side of a planar paper/card layer. The mechanism for vaporizing the payload may be selected accordingly. For the purposes of exemplifying aspects of the present disclosure, reference will be made to a cartomizer 30.

The vaporizer is for vaporizing a liquid (or more generally a payload) which comprises nicotine, and the cartomizer 30 may further include a wick or similar facility to transport a small amount of liquid from the reservoir to a vaporizing location on or adjacent the vaporizer. In the following, a heater is used as a specific example of a vaporizer. Optionally, as noted previously herein the heater may comprise a heating element driven by electrical resistance and positioned at a distance from the payload, and a heat conduction component that transfers heat from the heating element to the vaporizing location. However, it will be appreciated that other forms of vaporizer (for example, those which utilize ultrasonic waves) could also be used, and references to heater may be taken to incorporate other forms of vaporizer as appropriate.

The body 20 includes a re-chargeable cell or battery to provide power to the e-cigarette 10 and a circuit board for generally controlling the e-cigarette.

Conventionally, when the heater receives power from the battery, as controlled by the circuit board, the heater vaporizes the payload and this vapor is then inhaled by a user through the mouthpiece 35. In some specific embodiments the body is further provided with a manual activation device 265, e.g. a button, switch, or touch sensor located on the outside of the body.

As noted previously herein however, in order to be responsive to the user activation then typically the temperature of the heater has to be raised above the vaporization temperature of the payload very rapidly, which potentially requires a higher discharge or peak current, typically higher peak currents or discharge compromises overall battery capacity or effective capacity for a given cell geometry or chemistry.

Accordingly, in an embodiment of the present disclosure, the heater is pre-emptively preheated to a temperature below the vaporization temperature of the payload, so that a smaller differential temperature increase is then required to achieve vaporization in response to activation by the user. As a result, greater responsiveness can be achieved whilst avoiding the elevated drain on the battery associated with rapid heating from an ambient temperature to an operating temperature.

However this approach in turn has the potential to waste power by preheating the heater too early or when the user does not in fact subsequently activate the device; each such preheating action requires power from the battery and hence has the potential to use more power than is saved at the moment of activation itself.

It's therefore desirable to reduce the length of time that this preheating action occurs, and preferably also reduce the number of times the preheating action occurs in response to a false positive detection of imminent activation by the user.

Apparatus and methods to address or mitigate these problems are discussed later herein.

The body 20 and cartomizer 30 may be detachable from one another by separating in a direction parallel to the longitudinal axis LA, as shown in FIG. 1, but are joined together when the device 10 is in use by a connection, indicated schematically in FIG. 1 as 25A and 25B, to provide mechanical and electrical connectivity between the body 20 and the cartomizer 30. The electrical connector 25B on the body 20 that is used to connect to the cartomizer 30 also serves as a socket for connecting a charging device (not shown) when the body 20 is detached from the cartomizer 30. The other end of the charging device may be plugged into a USB socket to re-charge the cell in the body 20 of the e-cigarette 10. In other implementations, a cable may be provided for direct connection between the electrical connector 25B on the body 20 and a USB socket.

The e-cigarette 10 is provided with one or more holes (not shown in FIG. 1) for air inlets. These holes connect to an air passage through the e-cigarette 10 to the mouthpiece 35. When a user inhales through the mouthpiece 35, air is drawn into this air passage through the one or more air inlet holes, which are suitably located on the outside of the e-cigarette. When the heater is activated to vaporize the liquid from the cartridge, the airflow passes through, and combines with, the vapor, and this combination of airflow and vapor then passes out of the mouthpiece 35 to be inhaled by a user. Except in single-use devices, the cartomizer 30 may be detached from the body 20 and disposed of when the supply of liquid is exhausted (and replaced with another cartomizer if so desired).

It will be appreciated that the e-cigarette 10 shown in FIG. 1 is presented by way of example, and various other implementations can be adopted. For example, in some embodiments, the cartomizer 30 is provided as two separable components, namely a cartridge comprising the liquid reservoir and mouthpiece (which can be replaced when the liquid from the reservoir is exhausted), and a vaporizer comprising a heater (which is generally retained). As another example, the charging facility may connect to an additional or alternative power source, such as a car cigarette lighter.

Figure 2:
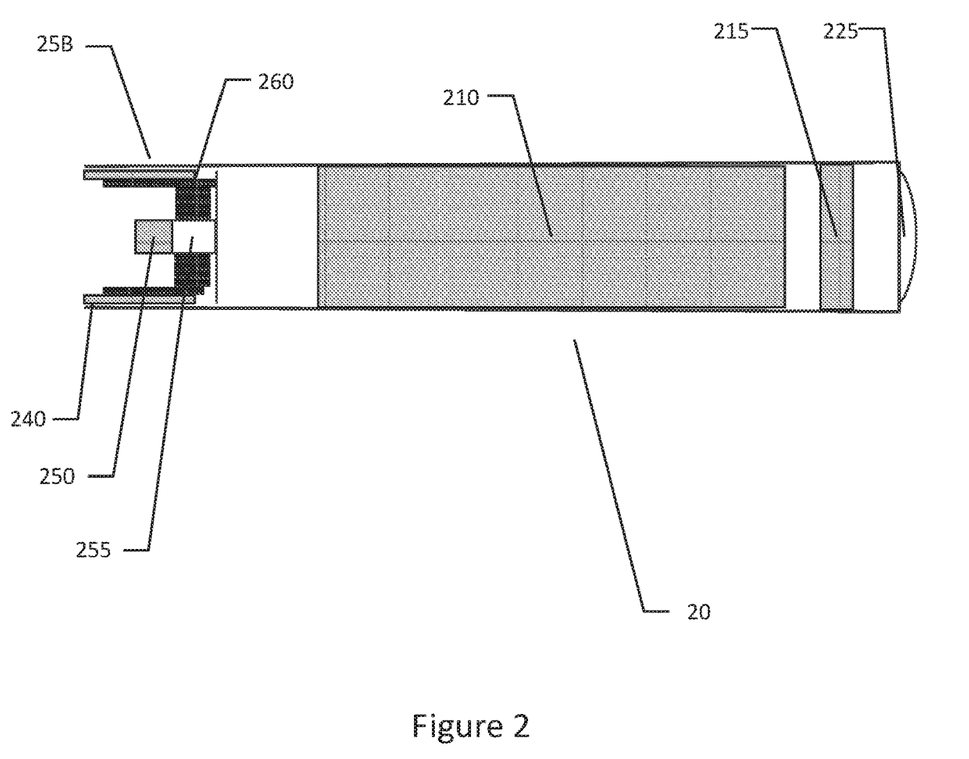
FIG. 2 is a schematic diagram of the body of the e-cigarette of FIG. 1 in accordance with some embodiments of the disclosure.

FIG. 2 is a schematic (simplified) diagram of the body 20 of the e-cigarette 10 of FIG. 1 in accordance with some embodiments of the disclosure. FIG. 2 can generally be regarded as a cross-section in a plane through the longitudinal axis LA of the e-cigarette 10. Note that various components and details of the body, e.g. such as wiring and more complex shaping, have been omitted from FIG. 2 for reasons of clarity.

The body 20 includes a battery or cell 210 for powering the e-cigarette 10 in response to a user activation of the device. Additionally, the body 20 includes a control unit (not shown in FIG. 2), for example a chip such as an application specific integrated circuit (ASIC) or microcontroller, for controlling the e-cigarette 10. The microcontroller or ASIC includes a CPU or micro-processor. The operations of the CPU and other electronic components are generally controlled at least in part by software programs running on the CPU (or other component). Such software programs may be stored in non-volatile memory, such as ROM, which can be integrated into the microcontroller itself, or provided as a separate component. The CPU may access the ROM to load and execute individual software programs as and when required. The microcontroller also contains appropriate communications interfaces (and control software) for communicating as appropriate with other devices in the body 10.

The body 20 further includes a cap 225 to seal and protect the far (distal) end of the e-cigarette 10. Typically there is an air inlet hole provided in or adjacent to the cap 225 to allow air to enter the body 20 when a user inhales on the mouthpiece 35. The control unit or ASIC may be positioned alongside or at one end of the battery 210. In some embodiments, the ASIC is attached to a sensor unit 215 to detect an inhalation on mouthpiece 35 (or alternatively the sensor unit 215 may be provided on the ASIC itself). An air path is provided from the air inlet through the e-cigarette, past the airflow sensor 215 and the heater (in the vaporizer or cartomizer 30), to the mouthpiece 35. Thus when a user inhales on the mouthpiece of the e-cigarette, the CPU detects such inhalation based on information from the airflow sensor 215. It will be appreciated therefore that the airflow sensor may act as an alternate or additional activation mechanism for the e-cigarette, when the user's inhalation generates a signal from the airflow sensor that is above a predetermined activation threshold.

Hence in more detail, the air flow sensor may be implemented in the device so that the user may activate the device and cause the control unit to supply power to the vaporizer to vaporize the payload by inhaling on the device. In these embodiments the user activation of the air flow sensor facilitates the user activation of the device. The body 20 includes the sensor unit 215 located in or adjacent to the air path through the body 20 from the air inlet to the air outlet (to the vaporizer). The sensor unit 215 may include a pressure drop sensor and temperature sensor (also in or adjacent to this air path). It will be appreciated, however, that the sensor unit 215 may include the pressure drop sensor without the temperature sensor or may include an airflow monitor to directly measure airflow (rather than pressure drop). Thus when a user inhales on the mouthpiece of the e-cigarette, the control unit detects such inhalation based on information from the pressure drop sensor. In response to the detection of an inhalation, the CPU supplies power to the heater, which thereby heats and vaporizes the payload for inhalation by the user.

At the opposite end of the body 20 from the cap 225 is the connector 25B for joining the body 20 to the cartomizer 30. The connector 25B provides mechanical and electrical connectivity between the body 20 and the cartomizer 30. The connector 25B includes a body connector 240, which is metallic (silver-plated in some embodiments) to serve as one terminal for electrical connection (positive or negative) to the cartomizer 30. The connector 25B further includes an electrical contact 250 to provide a second terminal for electrical connection to the cartomizer 30 of opposite polarity to the first terminal, namely body connector 240. The electrical contact 250 is mounted on a coil spring 255. When the body 20 is attached to the cartomizer 30, the connector 25A on the cartomizer 30 pushes against the electrical contact 250 in such a manner as to compress the coil spring in an axial direction, i.e. in a direction parallel to (co-aligned with) the longitudinal axis LA. In view of the resilient nature of the spring 255, this compression biases the spring 255 to expand, which has the effect of pushing the electrical contact 250 firmly against connector 25A of the cartomizer 30, thereby helping to ensure good electrical connectivity between the body 20 and the cartomizer 30. The body connector 240 and the electrical contact 250 are separated by a trestle 260, which is made of a non-conductor (such as plastic) to provide good insulation between the two electrical terminals. The trestle 260 is shaped to assist with the mutual mechanical engagement of connectors 25A and 25B.

As mentioned above, a button 265, which represents a form of manual activation device 265, may be located on the outer housing of the body 20. The button 265 may be implemented using any appropriate mechanism which is operable to be manually activated by the user—for example, as a mechanical button or switch, a capacitive or resistive touch sensor, and so on. It will also be appreciated that the manual activation device 265 may be located on the outer housing of the cartomizer 30, rather than the outer housing of the body 20, in which case, the manual activation device 265 may be attached to the ASIC via the connections 25A, 25B. The button 265 might also be located at the end of the body 20, in place of (or in addition to) cap 225.

Figure 3:
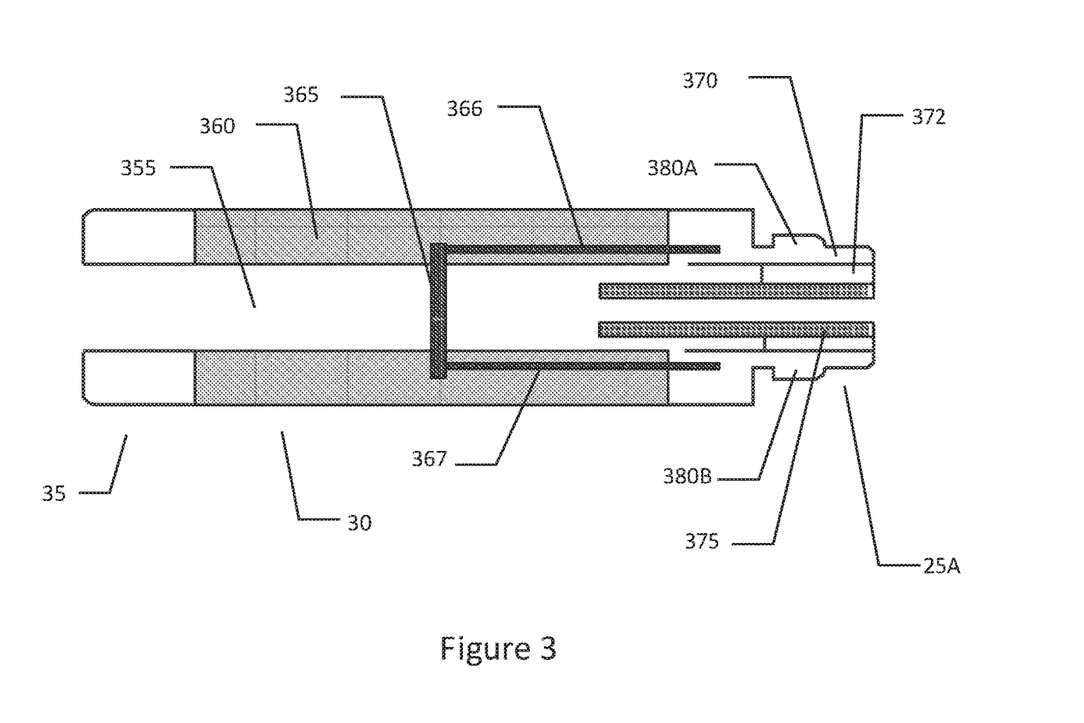
FIG. 3 is a schematic diagram of the vaporizer portion of the e-cigarette of FIG. 1 in accordance with some embodiments of the disclosure.

FIG. 3 is a schematic diagram of the cartomizer 30 of the e-cigarette 10 of FIG. 1 in accordance with some embodiments of the disclosure. FIG. 3 can generally be regarded as a cross-section in a plane through the longitudinal axis LA of the e-cigarette 10. Note that various components and details of the cartomizer 30, such as wiring and more complex shaping, have been omitted from FIG. 3 for reasons of clarity.

The cartomizer 30 includes an air passage 355 extending along the central (longitudinal) axis of the cartomizer 30 from the mouthpiece 35 to the connector 25A for joining the cartomizer 30 to the body 20. A reservoir of liquid 360 is provided around the air passage 335. This reservoir 360 may be implemented, for example, by providing cotton or foam soaked in liquid. The cartomizer 30 also includes a heater 365 for heating liquid from reservoir 360 to generate vapor to flow through air passage 355 and out through mouthpiece 35 in response to a user inhaling on the e-cigarette 10. The heater 365 is powered through lines 366 and 367, which are in turn connected to opposing polarities (positive and negative, or vice versa) of the battery 210 of the main body 20 via connector 25A (the details of the wiring between the power lines 366 and 367 and connector 25A are omitted from FIG. 3).

The connector 25A includes an inner electrode 375, which may be silver-plated or made of some other suitable metal or conducting material. When the cartomizer 30 is connected to the body 20, the inner electrode 375 contacts the electrical contact 250 of the body 20 to provide a first electrical path between the cartomizer 30 and the body 20. In particular, as the connectors 25A and 25B are engaged, the inner electrode 375 pushes against the electrical contact 250 so as to compress the coil spring 255, thereby helping to ensure good electrical contact between the inner electrode 375 and the electrical contact 250.

The inner electrode 375 is surrounded by an insulating ring 372, which may be made of plastic, rubber, silicone, or any other suitable material. The insulating ring is surrounded by the cartomizer connector 370, which may be silver-plated or made of some other suitable metal or conducting material. When the cartomizer 30 is connected to the body 20, the cartomizer connector 370 contacts the body connector 240 of the body 20 to provide a second electrical path between the cartomizer 30 and the body 20. In other words, the inner electrode 375 and the cartomizer connector 370 serve as positive and negative terminals (or vice versa) for supplying power from the battery 210 in the body 20 to the heater 365 in the cartomizer 30 via supply lines 366 and 367 as appropriate.

The cartomizer connector 370 is provided with two lugs or tabs 380A, 380B, which extend in opposite directions away from the longitudinal axis of the e-cigarette 10. These tabs are used to provide a bayonet fitting in conjunction with the body connector 240 for connecting the cartomizer 30 to the body 20. This bayonet fitting provides a secure and robust connection between the cartomizer 30 and the body 20, so that the cartomizer and body are held in a fixed position relative to one another, with minimal wobble or flexing, and the likelihood of any accidental disconnection is very small. At the same time, the bayonet fitting provides simple and rapid connection and disconnection by an insertion followed by a rotation for connection, and a rotation (in the reverse direction) followed by withdrawal for disconnection. It will be appreciated that other embodiments may use a different form of connection between the body 20 and the cartomizer 30, such as a snap fit or a screw connection.

Figure 4:
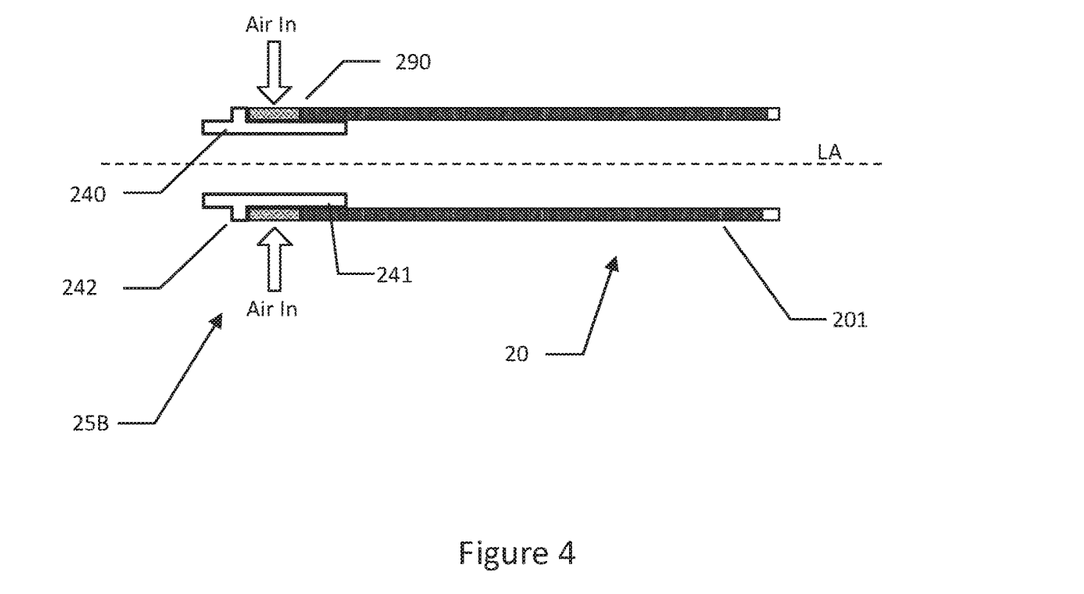
FIG. 4 is a schematic diagram showing certain aspects of one end of the body portion of the e-cigarette of FIG. 1 in accordance with some embodiments of the disclosure.

FIG. 4 is a schematic diagram of certain details of the connector 25B at the end of the body 20 in accordance with some embodiments of the disclosure (but omitting for clarity most of the internal structure of the connector as shown in FIG. 2, such as trestle 260). In particular, FIG. 4 shows the external housing 201 of the body 20, which generally has the form of a cylindrical tube. This external housing 201 may comprise, for example, an inner tube of metal with an outer covering of paper or similar. The external housing 201 may also comprise the manual activation device 265 (not shown in FIG. 4) so that the manual activation device 265 is easily accessible to the user.

The body connector 240 extends from this external housing 201 of the body 20. The body connector 240 as shown in FIG. 4 comprises two main portions, a shaft portion 241 in the shape of a hollow cylindrical tube, which is sized to fit just inside the external housing 201 of the body 20, and a lip portion 242 which is directed in a radially outward direction, away from the main longitudinal axis (LA) of the e-cigarette. Surrounding the shaft portion 241 of the body connector 240, where the shaft portion does not overlap with the external housing 201, is a collar or sleeve 290, which is again in a shape of a cylindrical tube. The collar 290 is retained between the lip portion 242 of the body connector 240 and the external housing 201 of the body, which together prevent movement of the collar 290 in an axial direction (i.e. parallel to axis LA). However, collar 290 is free to rotate around the shaft portion 241 (and hence also axis LA).

As mentioned above, the cap 225 is provided with an air inlet hole to allow air to flow when a user inhales on the mouthpiece 35. However, in some embodiments the majority of air that enters the device when a user inhales flows through collar 290 and body connector 240 as indicated by the two arrows in FIG. 4.

As noted previously herein, the e-cigarette of FIGS. 1-4 is illustrative example of an electronic vapor provision system but is non-limiting.

In an embodiment of the present invention, the e-cigarette may comprise one or more sensors. The sensors may take a number of different forms including the detection of a press activation in the form of the previously mentioned button 265, the detection of inhalation, for example by use of the previously mentioned inhalation (airflow) detector 215, one or more touch sensors (not shown), an accelerometer and/or gyroscopic sensor (not shown), a photoresistor, solar cell or other light sensitive sensor (not shown), a skin galvanic sensor (not shown), or any other sensor suited to the detection of an interaction by a user with the e-cigarette, such as an altimeter (not shown), or a camera (not shown).

As discussed previously, the heater takes an amount of time to heat up from its current ambient temperature to an operating temperature where the vaporization of the payload can occur. Consequently to minimize the amount of time between activation of the e-cigarette and vaporization of the payload, one can pre-heat the heater up to a temperature close to but below the vaporization temperature of the payload, so that the amount of time required to heat up the temperature from this near vaporization temperature to the operating temperature is much smaller than the time taken to heat up the heater from ambient temperature.

To a first approximation, one can assume an ambient temperature of around 15-30 degrees Celsius, as most people will keep their device about their person and will themselves be in this temperature range. Variabilities around this temperature can be assumed to be small compared to the vaporization temperature.

Clearly it is also desirable not to maintain the heater at the near vaporization temperature for longer than is necessary, as this drains power from the battery. Hence ideally pre-heating of the heater should begin at a time preceding activation of the e-cigarette equal to the amount of time required to heat up from ambient temperature to the near vaporization temperature.

The rate of change of temperature of the heating element as a function of current applied to it can be either calculated or determined empirically for the device, so that the time needed to reach a near vaporization temperature can be known in advance, calculated, or looked up in a table either from a presently measured temperature, or based on how long the heater has already been activated at a given current.

An ideal anticipation of activation by the user would provide the fastest response to activation with no additional drain on battery life. An earlier preheat drains battery life maintaining the heater at near vaporization temperature, whilst a later preheat increases the delay after activation before vaporization occurs.

As an alternative or addition to pre-heating the e-cigarette to a temperature just below the vaporization temperature, in an embodiment the device heats or further heats to an operable temperature and creates aerosol before the user is actively puffing on the device. In this case, the aerosol is effectively stored in a cavity of the device or within the consumable in anticipation of inhalation/activation.

Again an ideal anticipation of activation by the user would provide the fastest response to activation with no additional drain on battery life and, in this case, a maximum predetermined amount/period of vaporization corresponding to what can be held by the device before an unacceptable level of condensation occurs.

More generally, if the e-cigarette creates the desired aerosol over a longer period than would typically be acceptable by a user, then embodiments of the present disclosure may predict activation by the user so that the e-cigarette can generate the aerosol over potentially a longer period (e.g. through pre-heating and/or pre-vaporization as noted above) so that to the consumer the aerosol seems to be available on demand. The e-cigarette may then deliberately create the desired aerosol over a longer period in order to reduce the requirements from the battery such as peak current.

Embodiments of the present disclosure seek to approximate such ideal anticipation.

In an embodiment of the present disclosure, the control unit, operating under suitable software instruction, is adapted to preheat the heater to a temperature below the vaporization temperature of the payload at a point in time estimated to cause the heater to reach the near vaporization temperature at the moment of intentional activation of the e-cigarette by the user, so that the e-cigarette appears to be highly responsive, whilst limiting the amount of power used to maintain the heater at the near vaporization temperature before activation occurs.

To do this, the control unit is adapted to detect timing correlations between signals output from one or more sensors of the e-cigarette, and the moment of activation by the user.

Hence for example if the heater requires 0.3 seconds to reach near vaporization temperature under a preferred battery loading, and the user habitually brings the e-cigarette to their mouth 0.5 seconds before inhaling, then ideally the control unit can start preheating 0.2 seconds after the user brings the e-cigarette to their mouth.

The correlations between signals and the moment of activation by the user are likely to differ from user to user and are also likely to differ depending on the signal source, both in terms of their predictive worth and in terms of the timing variance between the relevant signal feature and the moment of activation.

Hence for example detecting from an accelerometer whether or not the e-cigarette is horizontal (as is likely to be the case when the user puts the e-cigarette in their mouth) may have a low correlation with activation for a user who keeps the e-cigarette lying flat in their handbag, but may have a high correlation with activation for a user who keeps their e-cigarette substantially vertical in their pocket. Consequently only in the second use case does the signal from the accelerometer have a potential predictive capability.

Meanwhile, in both cases accelerometer detection of a change in height, and/or an arcuate motion of the device associated with bending an elbow (e.g. indicative of the user bringing the device from approximately waist position to mouth position (may strongly correlate with activation for both of these users. Similarly a change of orientation together with a characteristic change in altitude associated with standing or recumbent use may also have a strong correlation with activation.

Consequently, a correlation threshold may optionally be used to discount certain signal sources. The correlation for a single source can be established by performing a cross-correlation between instances of the signal data (or specific features thereof, such as whether the e-cigarette is horizontal) and instances of activation by the user, with a time-out indicating non-activation. The cross-correlation can also be used to reveal the relative timings of the signal data (or specific signal feature) and the moment of activation by the user. Meanwhile the time-out (which is indicative of a negative correlation) may be a designer choice, such as 1, 5, 10, 30 or 60 seconds, and may differ between sensors.

However, even when there is overall an above-threshold correlation between a sensor signal feature and activation within the time-out window, the relative timings revealed by the cross-correlation may be so variable that they similarly affect the predictive power of a given signal.

Timing variability and hence the predictive worth of a signal for pre-emptively activating the heater may also differ from user to user and from signal source to signal source. For example if one user often talks with their e-cigarette in their mouth then there may be a high variability between when the e-cigarette becomes horizontal and when the user activates it, and hence a limited predictive value to the accelerometer signal. Meanwhile if another user only puts the e-cigarette in their mouth in order to use it, then there may be a much smaller variability and hence a greater predictive value to the accelerometer signal.

Hence it will be appreciated that different signals will have different predictive worth depending on how the individual user of the electronic vapor delivery system interacts with it ahead of intentionally activating the device for the purposes of inhalation.

Consequently the control unit is adapted to learn which preferred signals best predict when the user will activate the e-cigarette (i.e. automatically rank and/or select the signals as a function of correlation with activation and/or as a function of variability of signal feature timing with respect to the moment of activation), and use detection of the or each preferred signal to predict when activation of the device by the user to take place accordingly when to preheat the heater a pre-vaporization temperature is achieved as the user activates the device.

Hence for a given sensor or sensor set, for signals that meet a baseline correlation threshold, relative timing values may be stored for the last N instances where a signal feature has preceded activation of the device, and the mean and variance of those timing values may be calculated. N can be a small but statistically significant number of samples. Again, a variance threshold may be used to discount some signal sources.

Subsequently, the signals with the smallest timing variance may be chosen as the best indicator of when the user will activate the device, as they are measured to have the most reliable relationship between the signal feature and the moment of activation.

Accordingly, when the relevant signal feature from the relevant sensor is subsequently detected, the expected timing of the user's activation of the device can be predicted in response to the previously calculated relative timings between that signal feature and the user's activation of the device. Typically, this would be the mean timing value. However, it could be one standard deviation from the mean towards a longer time period, if improving the chances of reaching near-vaporization before activation was considered a priority (i.e. to reduce how often above-normal battery drain was required), or it could be one standard deviation from the mean towards a shorter time period, if reducing the chances of waiting at the near-vaporization before activation was considered a priority.

Variants

The following variants may be considered singly or in any suitable combination.

In a variant embodiment, different sensors may be used for selecting different states of the e-cigarette.

For example images from a camera on the e-cigarette, or on a smart phone paired to the e-cigarette, may be analyzed to determine an interaction with between the user and the e-cigarette. Physical interactions (for example in terms of relative positions of the users head, hand and/or e-cigarette) may be used to start the pre-heating process, whilst anticipatory interactions that do not involve (or are parallel to) physical interactions, such as a user's glance at the e-cigarette, their head orientation or mouth configuration, may optionally be limited to waking the device from a sleep state, or to transition from a pre-heat to pre-vaporization state, as appropriate (for example, when the user forms a mouth shape indicative of imminent engagement with the mouthpiece of the e-cigarette).

It was suggested previously herein that a correlation threshold could be applied to sensor signals to determine if there is a sufficiently strong correlation between a signal and subsequent activation of the device by the user. Hence in another variant embodiment, the correlation between two or more sensor signals and activation of the device may be considered.

For example, in the scenario described above where an e-cigarette is kept in a handbag that is regularly picked up and put down, the accelerometer alone may have a poor correlation with activation. However, when considered in conjunction with a signal from either a light sensor or touch sensor, then it may have a very good correlation with activation. Hence whether a sensor signal is evaluated for correlation and subsequently also for prediction may be made conditional upon another signal being present from another sensor, either at the same time or within a timing window that may be empirically determined.

As well as reinforcement, combinations of sensors can be used to prevent or reduce false-positives. Hence for example the accelerometer may have good correlation when in conjunction with detected skin contact (e.g. when not in the handbag), and so the correlation between acceleration and activation could be limited to when a touch sensor was active to prevent false positives.

In a similar manner, the correlation between one sensor signal and other contextual data and activation of the device may be considered.

For example, the accelerometer may provide good correlation with activation by itself at certain times of day or days of the week, for example when the user is at home or in the office and so is not regularly moving their handbag (or not keeping the e-cigarette in their handbag). Hence a sensor signal may be assessed differently at different times an/or in different places (for example via a paired mobile phone GPS), and different correlation profiles may be created accordingly for different user contexts such as home/work/travel/evenings/weekends, etc.

More generally the e-cigarette or a paired mobile device may look for combinations of signals/indicators optionally together with contexts to find those where there is a particularly high correlation between one or more signals and/or indicators, optionally for a given context, and activation. Examples such as those of the accelerometer with either a light sensor or a touch sensor, and the accelerometer at certain times or in certain locations, are merely non-limiting examples.

It will be appreciated that one of the strongest correlations with the smallest variances for activation by a user may be the start of an intake of breath, creating a measurable airflow before that airflow is at a level to trigger activation of the e-cigarette.

However, this signal is likely to occur very close to the actual activation of the device, because it is in fact part of a ramp-up to activation by the user.

Consequently the prediction provided by this signal feature may be too late to allow the heater to heat from ambient to near vaporization temperature without elevating the drain on (current from) the battery above a desired level.

Hence the control unit may instead select a second signal with the smallest timing variance whose indicated timing (mean or one standard deviation longer than the mean) is longer than the known or calculated heating time of the heater from ambient to near vaporization temperature within preferred battery operating conditions.

In this case, optionally, the control unit may heat the heater to a lower temperature in response to the second signal, where that lower temperature is chosen as one from which a transition to the near vaporization temperature can be achieved within the time between the detected start of intake of breath and the threshold airflow used to activate the device.

Figure 5A:
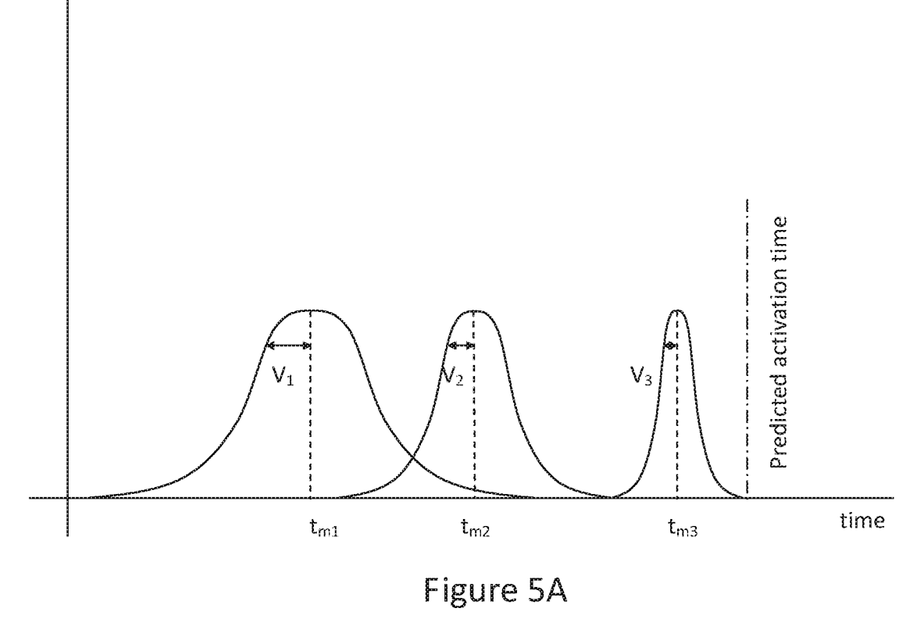
FIG. 5A illustrates the variance of signal features.
Figure 5B:
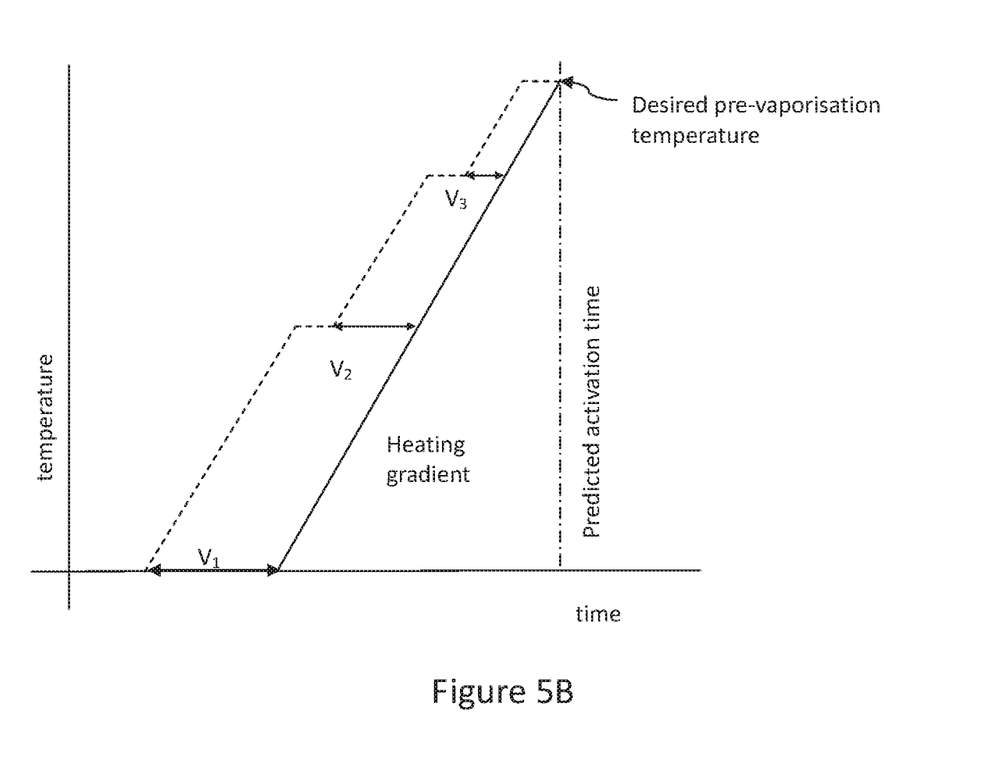
FIG. 5B illustrates the use of a variance measure to adjust pre-heating behavior in accordance with some embodiments of the disclosure.

Hence more generally and referring now to FIGS. 5A and 5B, where there are several signal features that meet the correlation and variance criteria, and where a signal feature that occurs after another has a smaller variance (i.e. where the predictive accuracy of these different signal features improve the closer they occur to the moment of activation), then a stepped pre-heating scheme may be used.

FIG. 5A has a horizontal time axis and an arbitrary signal axis, and shows the three different signals having mean timings $t_{m\#}$ relative to the predicted activation time, where earlier signals have a greater timing variability $V_\#$ than later signals.

FIG. 5B has a (different) time axis and a temperature axis, and shows a heating gradient for the heater from ambient to a desired near pre-vaporization temperature. It also shows an estimated start point for heating based on detection of the first signal, the start point being based upon the mean time between the first signal and use activation minus the time taken to heat the heater, further minus a value $V_1$ reflecting the variability of the signal. Consequently if only the first signal is detected, then the heater will follow the heating gradient and reach near vaporization temperature at a time preceding the predicted activation time corresponding to the value reflecting the variability of this signal.

Consequently, maintaining the heater at this pre-vaporization temperature for the period of time reflecting the variability of this first signal uses a comparatively large amount of power.

Accordingly, in this variant embodiment if the second signal is detected, then the timing for heating the heater is updated using a similar calculation based upon when the second signal was received, and its variability value $V_2$. Since its variability is smaller, the heating process may pause at an interim temperature before resuming. Maintaining this interim temperature will require less power than maintaining pre-vaporization temperature for the paused period of time.

Similarly if the third signal is detected, then the timing for the heater is updated again using a similar calculation based on when the first signal was received and its variability value $V_3$. Again the heating process may pause at an interim temperature before resuming and again maintaining this interim temperature will require less power than maintaining the pre-vaporization temperature for the paused period of time.

Consequently overall power is saved compared to merely heating the heater in response to the first signal. Furthermore it will be appreciated that the third signal and possibly the second signal may be received at a period of time sufficiently close to the predicted activation time that it would not be possible to heat the heater at the desired heating gradient from ambient temperature to the desired pre-vaporization temperature in time, so that these signals could not normally be used. However by preheating the heater to an interim temperature based upon a signal that occurs before it would be necessary to start heating at the desired heating gradient, it then becomes possible to use later signals for more accurate timing where the differential temperature between the current temperature and the desired pre-vaporization temperature can be achieved within the time available between the later signal and the predicted activation time.

Meanwhile it will be appreciated that if the second or third signals are not encountered, then the system may still preheat based on the first signal.

More generally, in this embodiment the time at which heating is started may not factor in the variance, but instead use the mean or some other timing relative to typical instances of a signal. In this case the timings of the specific instances of the three signals as they occur act to refine the predicted activation time, and optionally the heating gradient may be adjusted by changing the current so as to reach the desired pre-vaporization temperature at the predicted activation time as it is successively updated. However again it will be appreciated that the even if adjusted in response to a signal that occurs very close to activation, the heating gradient will be shallower when transitioning from an interim temperature to the desired pre-vaporization temperature than if attempting to heat the heater from ambient temperature to the desired pre-vaporization temperature, and hence drain on the battery is reduced.

Figure 6A:
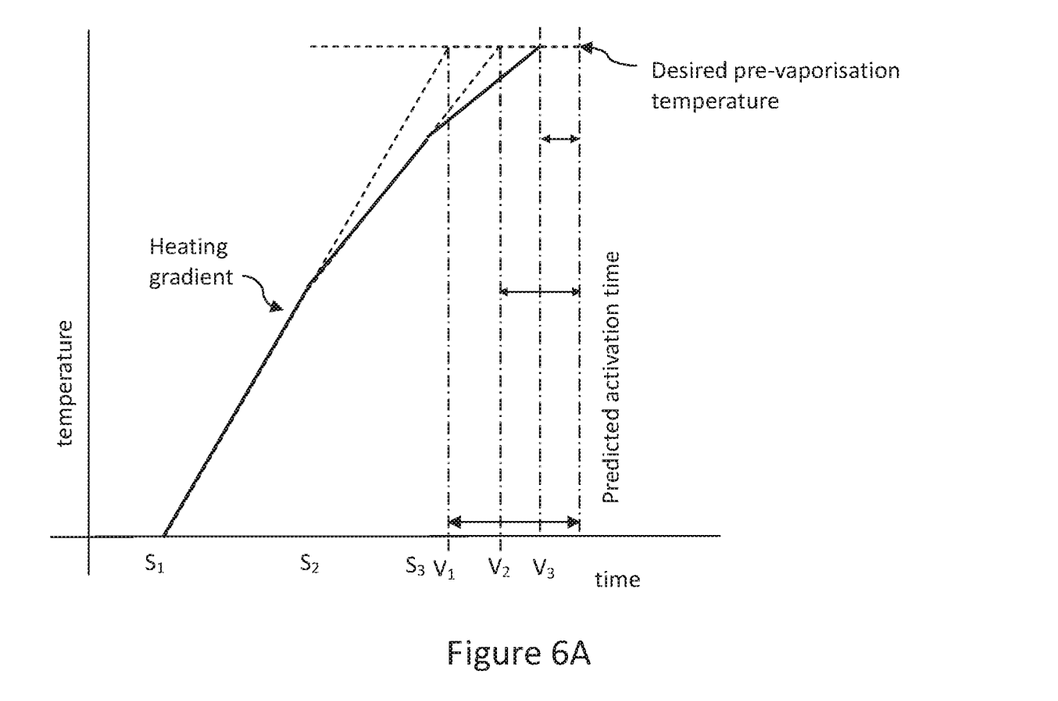
FIGS. 6A and 6B illustrate changes to a heating gradient in response to the occurrence of successive signal features in accordance with some embodiments of the disclosure.

Hence as shown in FIG. 6A when signal S1 is received, a predicted activation time with a variance correction related to signal S1 is calculated and heating begins at the default heating gradient. However, when signal S2 is received and the predicted activation time with a variance correction related to signal S2 is re-calculated, the heating is found to be in advance of the desired timing and so a lower gradient can be used. Again when signal S3 is received the predicted activation time with a variance correction related to signal S3 is re-calculated, and the heating is again found to be in advance of the desired timing and so a still lower gradient can be used.

Figure 6B:
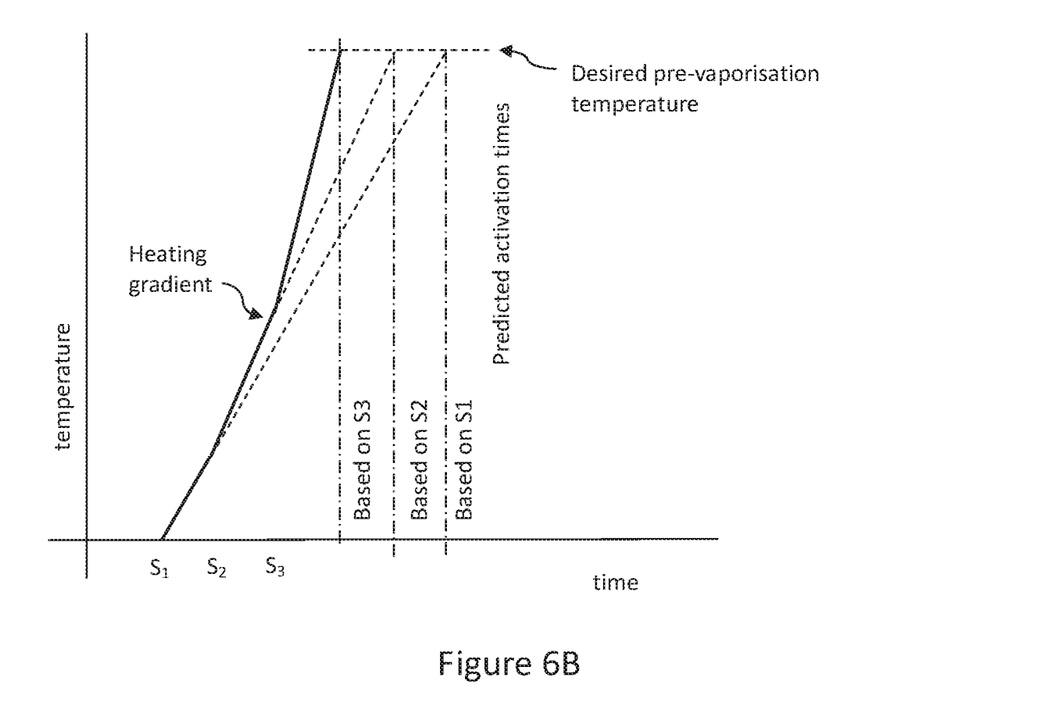

Meanwhile in FIG. 6B, when signal S1 is received, a predicted activation time (here optionally without a variance correction related to signal S1) is calculated and heating begins at the default heating gradient. However, if signal S2 is received and the predicted activation time is re-calculated, the heating in this example is found to be lagging behind the desired timing and so a higher gradient is used (but not as high as if heating from ambient after receiving signal S2). Similarly if signal S3 is received and the predicted activation time is re-calculated, the heating in this example is found to still be lagging behind the desired timing and so a yet higher gradient is used (but not as high as if heating from ambient after receiving signal S3).

In practice a mixture of increasing or decreasing the heating gradient may occur due to the variability of timing of individual signal events, whether the overall variance for a given signal source is factored into the timing of the heating or not.

In another variant embodiment, alternatively or in addition to any of the above techniques, a signal feature that has a correlation time that exceeds the default time-out (whether caused by a single event or a broadly periodic event) may be used to control a sensitivity window for the device. Hence for example if the user gets their e-cigarette out of their pocket typically 30 seconds before use, this may be too far in advance to start pre-heating in a way that is a net saver of electricity, but may be used to prime for receiving signal features for pre-heating evaluation purposes in a 60 second window immediately following, or between 10-50 seconds later, or between 20-40 seconds later, or between 25-35 seconds later, as appropriate; the specific timings are merely exemplary.

However such an approach is likely to reduce the instances of false positive signal detections and hence save power overall. This approach is also clearly related to the previously described approach of only considering the correlations of one signal feature in the presence of (or following within a certain time) another different signal feature, as in the example of the accelerometer and light detection signals.

The above described techniques refer to evaluation of correlation and optionally variance in calculating which signal feature(s) from which sensor(s) can be used to predict when the user will activate the e-cigarette, and time a pre-heating process accordingly.

However, in principle any statistical analysis technique may be used that can provide a predictive timing output based on a succession of example signal inputs.

Hence for example a Bayesian analysis may be used to predict the most likely activation time for a given signal or series of signals, and similarly an artificial neural network such as a so-called deep learning network (or any suitable network configuration) may be used.

However it is notable that the training time for such analyses and networks is typically very slow, requiring thousands of instances to learn. Hence a generic analysis/network may be provided that responds to signal features in ways that are most common within a training population of users, and this analysis/network may then be modified and personalized by exposure to use by the user.

Optionally a corpus of training data may be built up in this way (for example the last 100 interactions that resulted in an activation of the device) and these may be used a plurality of times to train the analysis/network when the device is otherwise idle, so that the training occurs more quickly.

Also with such analyses/networks, and also with the correlation/variance techniques described previously herein, multiple sets of statistics may be generated for different times of day, or for different days of the week. Hence for example usage patterns in the evenings and/or at weekends may differ compared to those during week days, and so the use of separate models may improve predictive accuracy.

In another variant embodiment, alternatively or in addition to any of the above techniques, optionally feedback data may be received relating to a property of the aerosol provided to the user at the subsequent user activation, and a future estimation of the user's expected moment of activation may then be adjusted based upon analysis of the feedback data. Hence feedback may be used to adjust the timing and/or temperature for the pre-emptive heating. This feedback may be from the user and/or from sensors within the device.

For example, user feedback can be obtained to rate the estimation process. Hence if the user inhales on the device and they do not receive enough aerosol (in terms of volume), this may be indicative of the estimating the user's time of activation as being later than it actually was. The user's feedback may be provided via a companion app on a mobile phone operable to communicate with the estimation processor, or via a local input means such as a button, slider or dial on the e-cigarette itself. Accordingly, based on the feedback, the estimation processor can update the estimation process for the next puff (e.g., in this case it can begin heating sooner/or at a higher power to generate more aerosol). This effectively serves to calibrate the estimation process. The user might calibrate the device in this way only if necessary, and hence this may be a mode that the user only engages with if the puff is not considered satisfactory.

Meanwhile alternatively or in addition, feedback may be provided by one or more sensors in the e-cigarette. For example, an airflow sensor can detect when inhalation has begun, and a further sensor may evaluate the density or other property of any aerosol flowing past it. Hence for example an optical sensor such as a standard light source and photosensor on opposing sides of a mouthpiece wall may be used to estimate aerosol density from the moment that inhalation is detected, to provide data relating to the promptness and quality of aerosol delivery to the user. Other sensors may be used instead of or in addition at appropriate points in the airflow path to assess if the aerosol is being produced to a predetermined standard. Hence for example a thermal sensor may be placed immediately downstream of the heater to detect whether airflow is hot enough to cause vaporization. Where aerosol density is initially insufficient or heating fails to raise the current ambient temperature air to an adequate level, data from these sensors may be fed back to the estimation processor and the estimation model can be updated accordingly.

It will be appreciated that the above techniques can be carried out by a processor of the e-cigarette under suitable software instruction. In this case, the electronic vapor provision system can be understood to be the e-cigarette alone.

Figure 7:
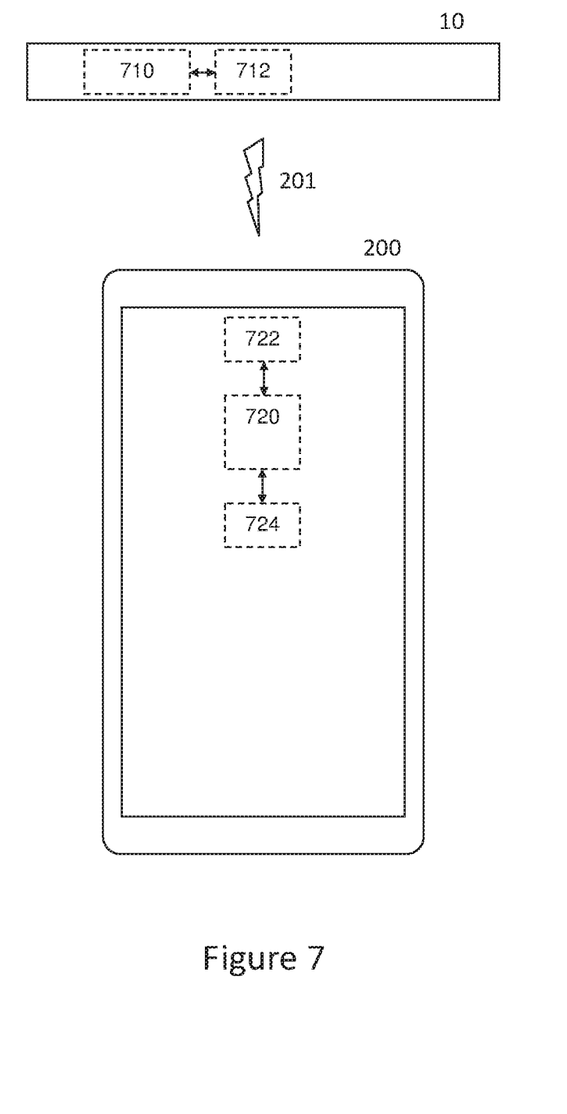
FIG. 7 is a schematic diagram showing an electronic vapor provision system in accordance with some embodiments of the disclosure.

However, referring now also to FIG. 7, optionally at least part of such a technique may be carried out by a mobile phone 200 or similar device in communication with the e-cigarette 10, for example via a Bluetooth® connection 201. In this case, the electronic vapor provision system can be understood to comprise both the e-cigarette and the mobile phone or similar device acting co-operatively.

Hence in this arrangement the control unit (710) of the e-cigarette, for example as part of the ASIC discussed previously herein, may communicate via a Bluetooth® transceiver 712 with the mobile phone 200. The mobile phone comprises a corresponding Bluetooth® transceiver 722 that relays data to the phone's processor 720. The processor itself implements techniques described herein under suitable software instruction from an app 724 or similar.

In this case maintenance of historical signal feature data (for example storing relative timings for N signal feature instances per sensor), and the calculation of correlations, means and variances or standard deviations may be performed by the mobile phone under suitable software instruction from the app. Data from the e-cigarette may be sent to the phone after each activation by the user, or collected by the e-cigarette and transmitted periodically (e.g. hourly or daily) depending on designer preference.

Optionally the mobile phone may also transmit signals to control the pre-heating of the heating element in response to sensor signals transmitted to it from the e-cigarette, but this may cause unacceptable delays in responsiveness and/or impose an unwanted battery drain in the e-cigarette due to transmission and reception. Hence alternatively the mobile phone can transmit data to the e-cigarette indicating which signal features can be used either singly or in combination (i.e. which signal features meet the correlation threshold either singly or in conjunction with other signal feature(s), together with a predicted time to activation (for example with respect to the mean timing for that signal feature, or taking into account variance in that signal feature, as described previously).

The e-cigarette can then use this information to calculate when to pre-heat the heater in response to the occurrence of a signal feature, such as the e-cigarette becoming horizontal, or touching the user's lips, or detecting skin resistance across two sides of the device, or signal features output by any other sensor whose values change during the course of interaction by the user with the device in preparation to use the device.

It will therefore be appreciated that the above methods and techniques may be carried out on conventional hardware (such as the above described e-cigarette, and optionally mobile phone) suitably adapted as applicable by software instruction or by the inclusion or substitution of dedicated hardware.

Thus the required adaptation to existing parts of a conventional equivalent device may be implemented in the form of a computer program product comprising processor implementable instructions stored on a non-transitory machine-readable medium such as a floppy disk, optical disk, hard disk, PROM, RAM, flash memory or any combination of these or other storage media, or realized in hardware as an ASIC (application specific integrated circuit) or an FPGA (field programmable gate array) or other configurable circuit suitable to use in adapting the conventional equivalent device. Separately, such a computer program may be transmitted via data signals on a network such as an Ethernet, a wireless network, the Internet, or any combination of these or other networks.

Advantageously, the above described embodiments act to reduce the energy supplied to the heater when pre-heating the heater to a near-vaporization temperature in advance of a puff by the user. As such, this may increase the number of puffs for a given battery capacity or present an opportunity to reduce the battery capacity of the device. The reduced length of the pre-vaporization heating phase potentially also reduces unwanted condensates on the internal walls of the device, improves puff count for a given amount of payload, and may also help to alleviate carbonyl build up, which can occur when the heater is on but there is no airflow in the device.

Thus, in a summary embodiment of the present disclosure there has been described an electronic vapor provision system (e.g. an e-cigarette 10 alone or in co-operation with a mobile phone 100) comprising a vaporizer for vaporizing a payload for inhalation by a user of the electronic vapor provision system, the vaporizer taking a finite period of time from having power supplied to it to vaporize the payload (whether a heater or an alternative system such as an ultrasonic vaporizer); a power supply (e.g. a battery, or potentially a fuel cell, capacitor or other power source) for supplying power to the vaporizer to vaporize the liquid payload in response to a user activation (for example by depression of a an activation button 265 or inhalation detected by a sensor 215 to be sufficient to meet an airflow or pressure drop threshold); one or more sensors (such as those described previously herein) operable to output respective signals in response to interaction of the user with the electronic vapor provision system; an estimation processor (for example e-cigarette controller 710 and/or mobile phone processor 720) configured (e.g. by suitable software instruction) to estimate a user's expected moment of activation, based upon analysis of one or more of the respective signals; and a control processor (for example e-cigarette controller 710) configured (e.g. by suitable software instruction) to cause power to be supplied to the vaporizer at a time that precedes the user's estimated expected moment of activation (for example by an amount of time calculated (or pre-calculated and retrieved) to raise the temperature of the heater to a near-vaporization temperature, in readiness for activation).

In an instance of this summary embodiment, the estimation processor calculates a correlation between signals from one or more sensors, and discounts signals from sensors that do not meet a respective correlation threshold.

In an instance of this summary embodiment the estimation processor calculates a timing variability of signals from one or more sensors with respect to subsequent user activation to generate a respective predicted timing for user activation relative to the detection of one or more respective signals.

In this case, the estimation processor may select a signal with the smallest variability as the preferred signal from which to select the predicted timing, for the case where two or more signals including the preferred signal are detected.

In an instance of the summary embodiment, the estimation processor selects successive signals as the signal from which to select the predicted timing, in the case where two or more signals are detected in succession, thereby updating the predicted timing.

In an instance of the summary embodiment, the estimation processor selects successive signals with smaller variabilities as the signal from which to select the predicted timing, in the case where two or more signals are detected in succession, thereby updating the predicted timing.

As appropriate, in an instance of the summary embodiment the vaporizer is a heater and the estimation processor calculates a pre-heating initiation time responsive to the or each predicted timing.

As appropriate, in an instance of the summary embodiment the vaporizer is a heater and the estimation processor calculates a heating gradient responsive to the or each predicted timing and the current temperature of the vaporizer.

And, in an instance of the summary embodiment, the electronic vapor provision comprises an e-cigarette comprising the control processor, and a mobile phone comprising the estimation processor.

Figure 8:
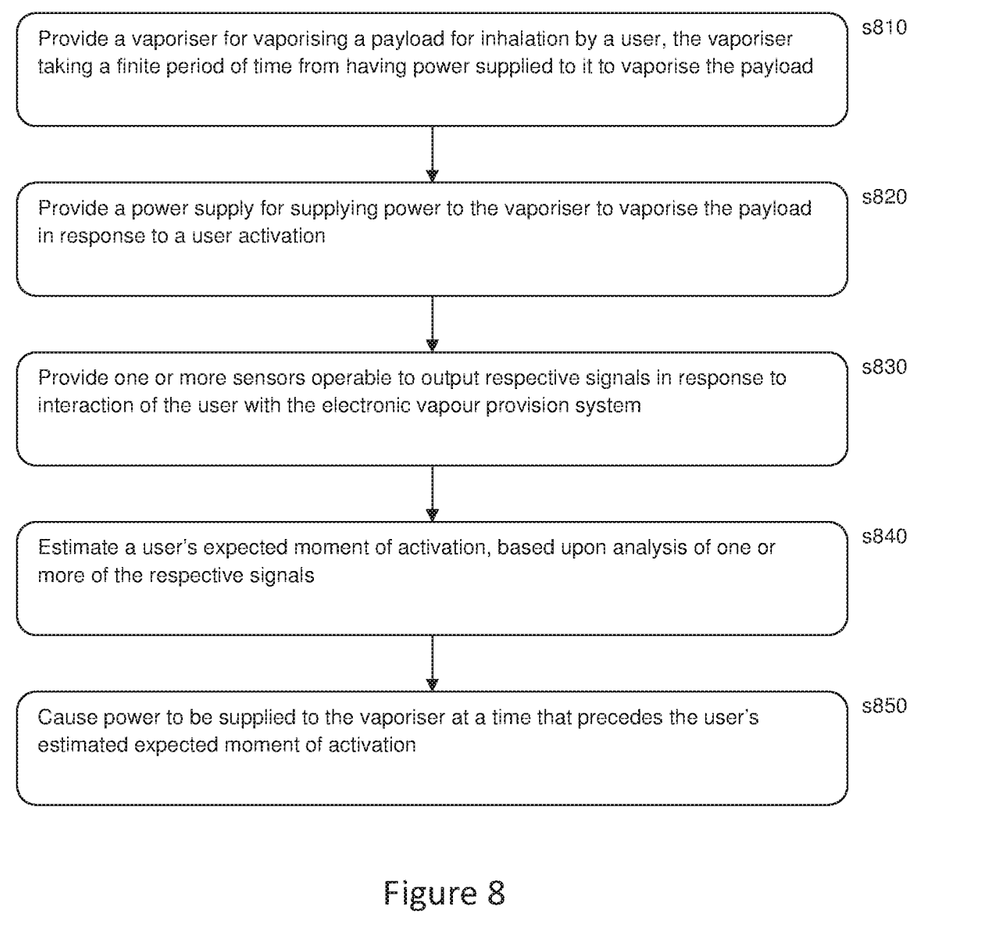
FIG. 8 is a flow diagram of a method of a method of vapor provision in accordance with some embodiments of the disclosure.

Similarly, referring now to FIG. 8, in a summary embodiment of the present disclosure, a method of vapor provision comprises:
  At s810, providing a vaporizer for vaporizing a payload for inhalation by a user, the vaporizer taking a finite period of time from having power supplied to it to vaporize the payload;
  At s820, providing a power supply for supplying power to the vaporizer to vaporize the payload in response to a user activation;
  At s830, providing one or more sensors operable to output respective signals in response to interaction of the user with the electronic vapor provision system;
  At s840, estimating a user's expected moment of activation, based upon analysis of one or more of the respective signals; and
  At s850, causing power to be supplied to the vaporizer at a time that precedes the user's estimated expected moment of activation.

It will be apparent to a person skilled in the art that variations in the above method corresponding to operation of the various embodiments of the apparatus as described and claimed herein are considered within the scope of the present invention, including but not limited to:
  the estimation comprising calculating a correlation between signals from one or more sensors, and discounting signals from sensors that do not meet a respective correlation threshold;
  the estimation comprising calculating a timing variability of signals from one or more sensors with respect to subsequent user activation, to generate a respective predicted timing for user activation relative to the detection of one or more respective signals;
  the estimation comprising selecting a signal with the smallest variability as the preferred signal from which to select the predicted timing, for the case where two or more signals including the preferred signal are detected;
  the estimation comprising selecting successive signals as the signal from which to select the predicted timing, in the case where two or more signals are detected in succession, thereby updating the predicted timing, or more specifically the estimation comprising selecting successive signals with smaller variabilities as the signal from which to select the predicted timing, in the case where two or more signals are detected in succession, thereby updating the predicted timing; and
  the vaporizer being a heater and the estimation comprising calculating a pre-heating initiation time responsive to the or each predicted timing, and/or calculating a heating gradient responsive to the or each predicted timing and the current temperature of the vaporizer.

While the above described embodiments have in some respects focused on some specific example aerosol provision systems, it will be appreciated the same principles can be applied for aerosol provision systems using other technologies. That is to say, the specific manner in which various aspects of the aerosol provision system function are not directly relevant to the principles underlying the examples described herein.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention (s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:
1. An electronic vapor provision system comprising:
  a vaporizer for vaporizing a payload for inhalation by a user of the electronic vapor provision system, the vaporizer taking a finite period of time from having power supplied to the vaporizer to vaporize the payload;
  a power supply for supplying power to the vaporizer to vaporize the payload in response to a user activation;
  one or more sensors operable to output respective signals in response to interaction of the user with the electronic vapor provision system;
  an estimation processor configured to estimate an expected moment of activation by the user, based upon analysis of one or more of the respective signals; and
  a control processor configured to cause power to be supplied to the vaporizer at a time that precedes the estimated expected moment of activation by the user.

2. The electronic vapor provision system of claim 1, wherein the estimation processor calculates a correlation between the respective signals from the one or more sensors, and discounts the respective signals from the one or more sensors that do not meet a respective correlation threshold.

3. The electronic vapor provision system of claim 1, wherein the estimation processor calculates a timing variability of the respective signals from the one or more sensors with respect to a subsequent user activation to generate a respective predicted timing for user activation relative to the detection of one or more respective signals.

4. The electronic vapor provision system of claim 3, wherein the estimation processor selects a signal with a smallest variability as a preferred signal from which to select the predicted timing, for a case where two or more signals including the preferred signal are detected.

5. The electronic vapor provision system of claim 3, wherein the estimation processor selects successive signals as a signal from which to select the predicted timing, in a case where two or more signals are detected in succession, thereby updating the predicted timing.

6. The electronic vapor provision system of claim 5, wherein the estimation processor selects successive signals with smaller variabilities as the signal from which to select the predicted timing, in the case where two or more signals are detected in succession, thereby updating the predicted timing.

7. The electronic vapor provision system of claim 3, wherein the vaporizer is a heater and the estimation processor calculates a pre-heating initiation time responsive to the or each predicted timing.

8. The electronic vapor provision system of claim 3, wherein the vaporizer is a heater and the estimation processor calculates a heating gradient responsive to the predicted timing and a current temperature of the vaporizer.

9. The electronic vapor provision system of claim 1, further comprising:
an e-cigarette comprising the control processor, and
a mobile phone comprising the estimation processor.

10. A method of vapor provision, comprising:
providing a vaporizer for vaporizing a payload for inhalation by a user, the vaporizer taking a finite period of time from having power supplied to the vaporizer to vaporize the payload;
providing a power supply for supplying power to the vaporizer to vaporize the payload in response to a user activation;
providing one or more sensors operable to output respective signals in response to interaction of the user with the electronic vapor provision system;
estimating an expected moment of activation by the user, based upon analysis of one or more of the respective signals; and
causing power to be supplied to the vaporizer at a time that precedes the estimated expected moment of activation by the user.

11. The method of claim 10, wherein the estimating comprises:
calculating a correlation between the respective signals from the one or more sensors, and
discounting the respective signals from the one or more sensors that do not meet a respective correlation threshold.

12. The method of claim 10, wherein the estimating further comprises calculating a timing variability of the respective signals from the one or more sensors with respect to a subsequent user activation, to generate a respective predicted timing for user activation relative to detection of one or more respective signals.

13. The method of claim 12, wherein the estimating further comprises selecting a signal with a smallest variability as a preferred signal from which to select the predicted timing, for a case where two or more signals including the preferred signal are detected.

14. The method of claim 12, wherein the estimating further comprises selecting successive signals as a signal from which to select the predicted timing, in a case where two or more signals are detected in succession, thereby updating the predicted timing.

15. The method of claim 14, wherein the estimating further comprises selecting successive signals with smaller variabilities as the signal from which to select the predicted timing, in the case where two or more signals are detected in succession, thereby updating the predicted timing.

16. The method of claim 10, wherein the estimating further comprises:
receiving feedback data relating to a property of an aerosol provided to the user at the subsequent user activation, and
adjusting future estimation of the expected moment of activation by the user, based upon analysis of the feedback data.

17. The method of claim 12, wherein the vaporizer is a heater and the estimating further comprises calculating a pre-heating initiation time responsive to the predicted timing.

18. The method of claim 12, wherein the vaporizer is a heater and the estimating further comprises calculating a heating gradient responsive to the predicted timing and a current temperature of the vaporizer.

19. A non-transitory computer readable storage medium storing computer executable instructions adapted to, when loaded onto and executed by a computer system, cause the computer system to perform the method of claim 10.

* * * * *